US008158369B2

(12) United States Patent
Ono et al.

(10) Patent No.: US 8,158,369 B2
(45) Date of Patent: Apr. 17, 2012

(54) CANCER DIAGNOSTIC KIT AND CANCER DIAGNOSTIC METHOD

(75) Inventors: Toshiro Ono, Okayama (JP); Eiichi Nakayama, Okayama (JP)

(73) Assignee: National University Corporation Okayama University, Okayama (JP)

(*) Notice: Subject to any disclaimer, the term of this patent is extended or adjusted under 35 U.S.C. 154(b) by 76 days.

(21) Appl. No.: 12/677,755

(22) PCT Filed: Jul. 18, 2008

(86) PCT No.: PCT/JP2008/063002
§ 371 (c)(1),
(2), (4) Date: Mar. 11, 2010

(87) PCT Pub. No.: WO2009/034779
PCT Pub. Date: Mar. 19, 2009

(65) Prior Publication Data
US 2010/0248234 A1 Sep. 30, 2010

(30) Foreign Application Priority Data
Sep. 12, 2007 (JP) .................................. 2007-236048

(51) Int. Cl.
G01N 33/53 (2006.01)
G01N 33/567 (2006.01)
G01N 33/574 (2006.01)
C07K 14/00 (2006.01)
(52) U.S. Cl. ........ 435/7.1; 435/7.21; 435/7.23; 530/350
(58) Field of Classification Search .................... None
See application file for complete search history.

(56) References Cited

U.S. PATENT DOCUMENTS
2005/0272080 A1 12/2005 Palma et al.

FOREIGN PATENT DOCUMENTS
| EP | 1 347 046 A1 | 9/2003 |
| EP | 1 440 981 A2 | 7/2004 |
| WO | WO-02/078526 A2 | 10/2002 |
| WO | WO-03/064593 A2 | 8/2003 |

OTHER PUBLICATIONS

GenBank Accession No. BC060796 (NCBI Jul. 17, 2006).*
Taber's Cyclopedic Medical Dictionary (1985, F.A. Davis Company, Philadelphia, p. 274).*
Busken, C et al. (Digestive Disease Week Abstracts and Itinerary Planner, 2003, abstract No:850).*
Kaiser (Science, 2006, 313: 1370).*
Krontiris and Capizzi (Internal Medicine, 4th Edition, Editor-in-chief Jay Stein, Elsevier Science, 1994 Chapters 71-72, pp. 699-729).*
NCI Dictionary of Cancer Terms-National Cancer Institute (skin cancer, www.cancer.gov/dictionary, Oct. 6, 2011).*
Sjoblom et al., "The consensus coding sequences of human breast and colorectal cancers," Science vol. 314, pp. 268-274 and Table S4 (2006).
Li, et al., "A novel testis specific protein (TSP-NY) gene from adult testis," NCBI Entrez Nucleotide, Accession No. NM_032573 (GI:14211886), May 29, 2001.
Strausbert, et al., "Generation and Initial Analysis of More than 15,000 full-length human and mouse cDNA sequences " NCBI Entrez Nucleotide, Accession No. NM_201435 (GI: 42475943), Feb. 9, 2004.
Mizukami, et al., "Possibilities of Antibody Treatment against Lung Cancer Antigen Identified by SEREX," Second Department of Surgery, School of Medicine, University of Occupational and Environmental Health, Japan, W3-4, Biotherapy, vol. 18, No. suppl. 1, p. 55 (2004).
Mizukami, et al., "Study of Change in Serum Antibody Titer Against Lung Cancer Antigen Identified by SEREX," Second Department of Surgery, School of Medicine, University of Occupational and Environmental Health, Japan, Journal of Japan Society of Clinical Oncology, vol. 39, No. 2, p. 790 (2004).
Van der Bruggen, et al., "A gene encoding an Antigen Recognized by Cytolytic T Lymphocytes on a Human Melanoma," Science vol. 254, pp. 1643-1647 (1991).
Gure, et al., "SSX: A Multigene Family with Several Members Transcribed in Normal Testis and Human Cancer " Int. J. Cancer vol. 72, pp. 965-971 (1997).
Chen, et al., "A testicular antigen aberrantly expressed in human cancers detected by autologous antibody screening" Proc. Natl. Acad. Sci. USA vol. 94, p. 1914-1918 (1997).
Jager, et al., "Induction of primary NY-ESO-1 immunity: CD8+T lymphocyte and antibody responses in peptide-vaccinated patients with NY-ESO-1 + cancers" Proc. Natl. Acad. Sci. USA vol. 97, pp. 12198-12203 (2000).
Stockert, et al., "A survey of the humoral immune response of cancer patients to a panel of human tumor antigens" J. Exp. Med. vol. 187, pp. 1349-1354 (1998).
Kurashige, et al. "NY-ES0-1 expression and immunogenicity associated with transitional cell carcinoma: correlation with tumor grade" Cancer Res. vol. 61, pp. 4671-4674 (2001).
Nakada, et al., "NY-ESO-1 mRNA expression and immunogenicity in advanced prostate cancer" Cancer Immunity, 3:10 (2003).
Sugita, et al., "NY-ESO-1 expression and immunogenicity in malignant and benign breast tumors" Cancer Res. vol. 64, pp. 2199-2204 (2004).
Fujita, et al., "NY-ESO-1 expression and immunogenicity in Esophageal Cancer" Cancer Res. vol. 10, pp. 6551-6558 (2004).
Nakamura, et al., "Expression and Immunogenicity of NY-ESO-1 in hepatocellular carcinoma" J. Gastroenterol. Hepatol. vol. 21, pp. 1281-1285 (2006).

(Continued)

*Primary Examiner* — Peter J Reddig
(74) *Attorney, Agent, or Firm* — Edwards Wildman Palmer LLP; David G. Conlin; Lisa Swiszcz

(57) ABSTRACT

The present invention provides a kit and method for diagnosing a cancer using a polynucleotide including a nucleotide sequence of SEQ ID No: 1 or 3 or a partial sequence thereof, a polypeptide consisting of an amino acid sequence of SEQ ID No: 2 or 4 or a partial sequence thereof, or an antibody binding specifically to a polypeptide consisting of an amino acid sequence of SEQ ID No: 2 or 4 or a partial sequence thereof. This makes it possible to find a CT antigen useful for testing, diagnosis, or treatment of a digestive system cancer and to develop a novel cancer diagnostic technique using the CT antigen.

5 Claims, 5 Drawing Sheets

OTHER PUBLICATIONS

Sahin, et al., "Human Neoplasms elicit multiple specific immune responses in the autologous host" Proc. Natl. Acad. Sci. USA, Dec. vol. 92, 11810-11813 (1995).

Supplementary European Search Report (Application No. EP 08 79 1311) as mailed Aug. 3, 2010.

Database EM_HUM (Online), Apr. 23, 2003, Shan YX and Yu L, "Cloning and characterization of a novel gene highly expressed in testis" (XP002592988).

Database EM_HUM (Online) Nov. 5, 2003, Strausberg R L et al., "*Homo sapiens* coiled-coil domain containing 62, mRNA" (XP002592989).

Database UniProt (Online) Jun. 13, 2006, Shan YX and Yu L, "CCD62 Human" (XP002592987).

Odunsi, Kunle et al., "NY-ESO-1 and LAGE-1 Cancer-Testis Antigens Are Potential Targets for Immunotherapy in Epithelial Ovarian Cancer", Cancer Research, American Association for Cancer Research, US, vol. 63, No. 18, Sep. 15, 2003, pp. 6076-6083.

Domae, Shohei et al., "Identification of CCDC62-2 as a novel cancer/testis antigen and its immunogenicity", International Journal of Cancer, vol. 124, Dec. 11, 2008, pp. 2347-2352.

Supplemental European Search Report for European Application No. EP 08 79 1311.

* cited by examiner (a) RT-PCR (b) Real-Time RT-PCR (a) LUNG CANCER (b) COLON CANCER (c) PROSTATIC CANCER 1 CCDC62 (variant 2)
2 CCDC62 (variant 1)
3 OY-ST-2 (clone 1)
4 OY-ST-2 (clone 2)
5 GKAP1
6 Negative clone

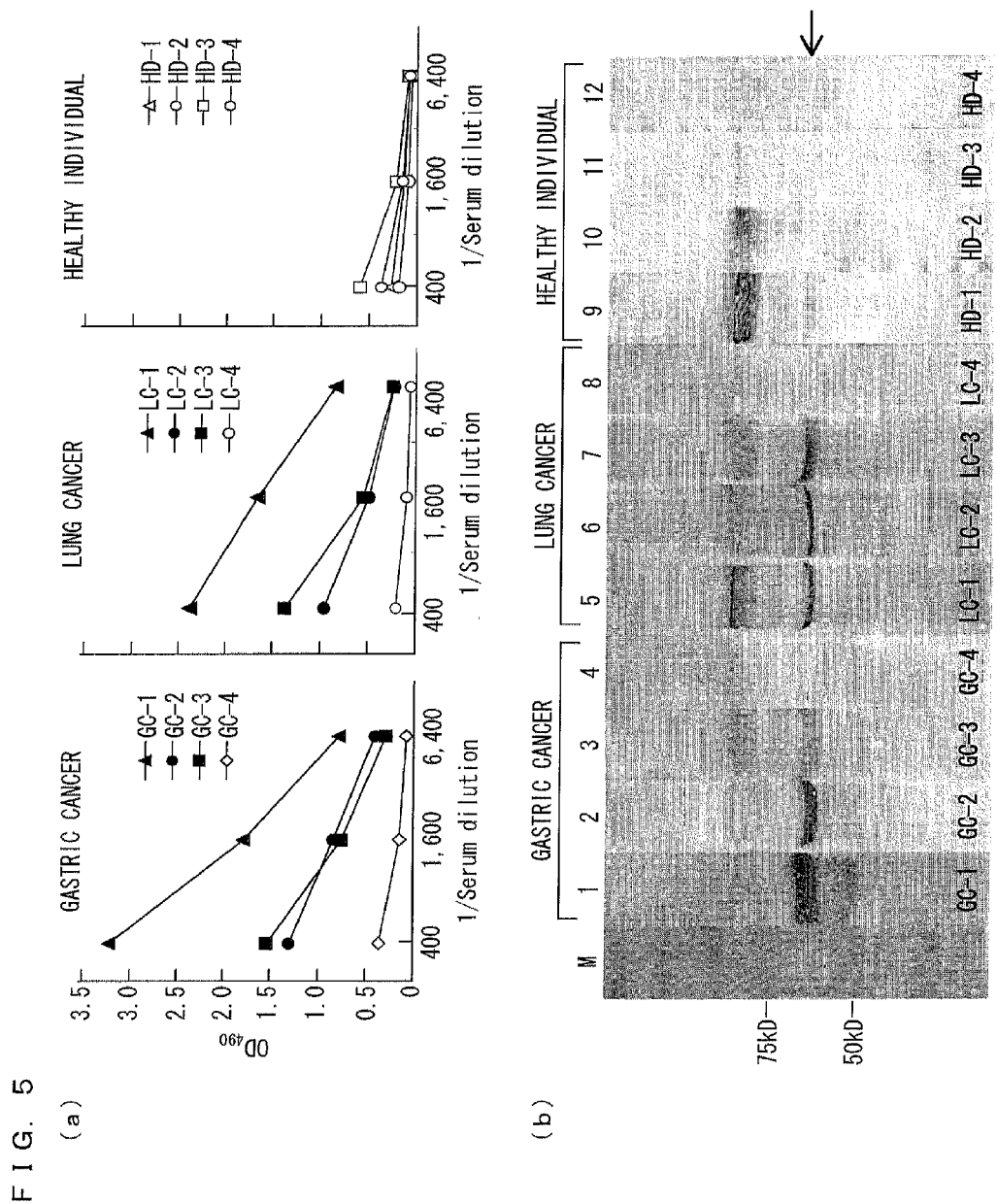

CANCER DIAGNOSTIC KIT AND CANCER DIAGNOSTIC METHOD

CROSS-REFERENCE TO RELATED APPLICATIONS

This application is the national stage application pursuant to 35 U.S.C. §371 of PCT International Application No. PCT/JP2008/063002, filed Jul. 18, 2008, which claims priority to Japanese patent application no. 236048/2007, filed Sep. 12, 2007. The contents of these applications are incorporated herein by reference in their entirety.

TECHNICAL FIELD

The present invention relates to a novel cancer diagnostic technique. More specifically, the present invention relates to a kit and method for diagnosing a cancer both of which uses the expression of CCDC62 or the presence of an anti-CCDC62 antibody as an index.

BACKGROUND ART

In order to establish a testing method, diagnostic method, and therapeutic method effective to cancers, it is necessary to find out a cancer antigen that expresses in an objective cancer with high frequency and has high antigenicity. However, there are few cancer antigens useful for testing, diagnosis, or treatment of digestive system cancers, especially gastric cancer and colon cancer. Therefore, it is very important to develop useful cancer antigens for testing, diagnosis, or treatment of digestive system cancers.

In terms of accompanying side effects, the most useful antigen for testing, diagnosis, or treatment of human cancer is considered to be a cancer-testis antigen (hereinafter referred to as "CT antigen") that expresses in various cancers, but are confined to testis among normal tissues. To date, about 40 kinds of CT antigens have been identified and reported. However, all of these CT antigens do not possess strong immunogenicity to cancer patients, and there are a limited number of CT antigens promising for diagnosis marker of cancers, test marker of cancers, or treatment of cancers.

Typical CT antigens that have been reported to date include MAGE (see Non Patent Literature 1), SSX (see Non Patent Literature 2), and NY-ESO-1 (see Non Patent Literature 3). MAGE and NY-ESO-1 have been applied in clinical settings in the world, particularly in Europe and the United States, and the clinical settings have achieved some positive results (for example, for clinical application of NY-ESO-1, see Non Patent Literature 4). Thus, it can be said that NY-ESO-1 is currently the most promising CT antigen for applications to treatment of cancer and the like.

Non Patent Literature 1 van der Bruggen P, Traversari C, Chomez P, Lurquin C, De Plaen E, van den Eynde B, Knuth A, Boon T. A gene encoding an antigen recognized by cytolytic T lymphocytes on a human melanoma. Science 254: 1643-1647, 1991.

Non Patent Literature 2

Gure A O, Tureci O, Sahin U, Tsang S, Scanlan M J, Jager E, Knuth A, Pfreundschuh M, Old L J, Chen Y T. SSX: a multigene family with several members transcribed in normal testis and human cancer. Int. J. Cancer 72: 965-971, 1997.

Non Patent Literature 3

Chen Y T, Scanlan, M J, Sahin U, Tureci O, Gure A O, Tsang S, Williamson B, Stockert E, Pfreundschuh M, Old L J. A testicular antigen aberrantly expressed in human cancers detected by autologous antibody screening. Proc. Natl. Acad. Sci. USA 94: 1914-1918, 1997.

Non Patent Literature 4

Jager E, Gnjatic S, Nagata Y, Stockert E, Jager D, Karbach J, Neumann A, Rieckenberg J, Chen Y T, Ritter G, Hoffman E, Arand M, Old L J, Knuth A. Induction of primary NY-ESO-1 immunity: CD8+ T lymphocyte and antibody responses in peptide-vaccinated patients with NY-ESO-1+ cancers. Proc. Natl. Acad. Sci. USA 97: 12198-12203, 2000.

Non Patent Literature 5

Stockert E, Jager E, Chen Y T, Scanlan M J, Gout I, Karbach J, Arand M, Knuth A, Old L J. A survey of the humoral immune response of cancer patients to a panel of human tumor antigens. J. Exp. Med. 187: 1349-1354, 1998.

Non Patent Literature 6

Kurashige T, Noguchi Y, Saika T, Ono T, Nagata Y, Jungbluth A A, Ritter G, Chen Y T, Stockert E, Tsushima T, Kumon H, Old L J, Nakayama E. NY-ESO-1 expression and immunogenicity associated with transitional cell carcinoma: correlation with tumor grade. Cancer Res. 61: 4671-4674, 2001.

Non Patent Literature 7

Nakada T, Noguchi Y, Sato S, Ono T, Saika T, Kurashige T, Gnjatic S, Ritter G, Chen Y T, Stockert E, Nasu Y, Tsushima T, Kumon H, Old L J, Nakayama E. NY-ESO-1 mRNA expression and immunogenicity in advanced prostate cancer. Cancer Immunity 3: 10, 2003.

Non Patent Literature 8

Sugita Y, Wada S, Fujita S, Nakata T, Sato S, Noguchi Y, Jungbluth A A, Yamaguchi M, Chen Y T, Stockert E, Gnjatic S, Williamson B, Scanlan M J, Ono T, Sakita I, Yasui M, Miyoshi Y, Tamaki Y, Matsuura N, Noguchi S, Old L J, Nakayama E, Monden M. NY-ESO-1 expression and immunogenicity in malignant and benign breast tumors. Cancer Res. 64: 2199-2204, 2004.

Non Patent Literature 9

Fujita S, Wada H, Jungbluth A A. Sato S, Nakata T, Noguchi Y, Doki Y, Yasui M, Sugita Y, Yasuda T, Yano M, Ono T, Chen Y T, Higashiyama M, Gnjatic S, Old L J, Nakayama E, Monden M. NY-ESO-1 expression and immunogenicity in esophageal cancer. Clin. Cancer Res. 10: 6551-6558, 2004.

Non Patent Literature 10

Nakamura, S, Nouso K, Noguchi Y, Higashi T, Ono T, Jungbluth A A, Chen Y T, Old L J, Nakayama E, Shiratori Y. Expression and immunogenicity of NY-ESO-1 in hepatocellular carcinoma. J. Gastroenterol. Hepatol. 21: 1281-1285, 2006.

SUMMARY OF INVENTION

The inventors of the present invention tested patients with various epithelial tumors for their capabilities of producing antibodies to NY-ESO-1. The result of the test was as follows: 7% for bladder cancer (9 of 124 cases, see Non Patent Literature 6), 4.6% for prostatic cancer (10 of 218 cases, see Non Patent Literature 7), 1.6% for breast cancer (1 of 62 cases, see Non Patent Literature 8), 3.9% (2 of 51 cases, see Non Patent Literature 9), 2.2% for liver cancer (2 of 92 cases, see Non Patent Literature 10). This reveals that the capabilities of producing antibodies are not so high in all these cancers. Thus, antibodies against the CT antigens reported in the past exist in sera from patients with epithelial tumor with extremely low frequency.

Further, in some rare cases, the CT antigens reported in the past express in digestive system cancers such as gastric cancer and colon cancer. Moreover, the antibodies against the CT antigens are produced with extremely low frequency in patients with digestive system cancers. For example, it has been reported that the capabilities of producing antibodies to NY-ESO-1, MAGE, and SSX of patients with colon cancer are all 0% (see Non Patent Literature 5). Incidentally, the inventors of the present invention tested sera from 58 patients with colon cancer for their capabilities of producing antibodies to NY-ESO-1. The result of the test showed that the capabilities of producing antibodies to NY-ESO-1 were 0% (not published). Further, even in the preliminary analysis using sera from patients with gastric cancer by the inventors of the present invention, the presence of the antibody to NY-ESO-1 has not been proved yet.

Thus, it is not easy to find out a useful cancer antigen for diagnosis of epithelial tumors including digestive system cancers, such as gastric cancer and colon cancer. Therefore, there is a very strong demand for the development of a useful cancer antigen for diagnosis of digestive system cancers.

The present invention has been attained in view of the above problem, and an object of the present invention is to provide a novel cancer diagnostic technique using a useful cancer antigen (preferably CT antigen) for testing, diagnosis, or treatment of epithelial tumors including digestive system cancers.

In order to solve the above problem, the inventors of the present invention carried out SEREX (serological analysis of cancer antigens by recombinant cDNA expression cloning) using a cDNA library derived from normal testis and a serum from a patient with gastric cancer. Then, the inventors of the present invention accomplished the present invention by finding that CCDC62 in an antibody-positive clone is a CT antigen.

That is, a kit according to the present invention is a kit for diagnosing a cancer, comprising a polynucleotide including a nucleotide sequence of SEQ ID No: 1 or 3 or a partial sequence thereof.

A kit according to the present invention is a kit for diagnosing a cancer, comprising a polypeptide consisting of an amino acid sequence of SEQ ID No: 2 or 4 or a partial sequence thereof.

A kit according to the present invention is a kit for diagnosing a cancer, comprising an antibody binding specifically to a polypeptide consisting of an amino acid sequence of SEQ ID No: 2 or 4 or a partial sequence thereof.

A kit according to the present invention is preferably used for diagnosis of an epithelial tumor or a skin cancer, more preferably for diagnosis of at least one cancer selected from the group consisting of a gastric cancer, a colon cancer, a breast cancer, a head and neck cancer, a lung cancer, a renal cancer, a prostatic cancer, and a malignant melanoma.

A method for diagnosing a cancer according to the present invention is characterized by comprising a polynucleotide measuring step of measuring a level of presence of a polynucleotide including a nucleotide sequence of SEQ ID No: 1 or 3 or a partial sequence thereof in a sample derived from a subject.

A method for diagnosing a cancer according to the present invention is characterized by comprising: a polypeptide measuring step of measuring a level of presence of a polypeptide consisting of an amino acid sequence of SEQ ID No: 2 or 4 or a partial sequence thereof in a sample derived from a subject.

A method for diagnosing a cancer according to the present invention is characterized by comprising: an antibody measuring step of measuring a level of an antibody binding specifically to a polypeptide consisting of an amino acid sequence of SEQ ID No: 2 or 4 or a partial sequence thereof in a sample derived from a subject.

A method for diagnosing a cancer according to the present invention is preferably used for diagnosis of an epithelial tumor or a skin cancer, more preferably for diagnosis of at least one cancer selected from the group consisting of a gastric cancer, a colon cancer, a breast cancer, a head and neck cancer, a lung cancer, a renal cancer, a prostatic cancer, and a malignant melanoma.

Additional objects, features, and strengths of the present invention will be made clear by the description below. Further, the advantages of the present invention will be evident from the following explanation in reference to the drawings.

BRIEF DESCRIPTION OF DRAWINGS

FIG. 5 is a view showing the result of analysis of humoral immune responses of cancer patients against CCDC62-2 protein, wherein (a) shows the result of ELISA analysis and (b) shows the result of Western blotting analysis.

DESCRIPTION OF EMBODIMENTS

Figure 1:
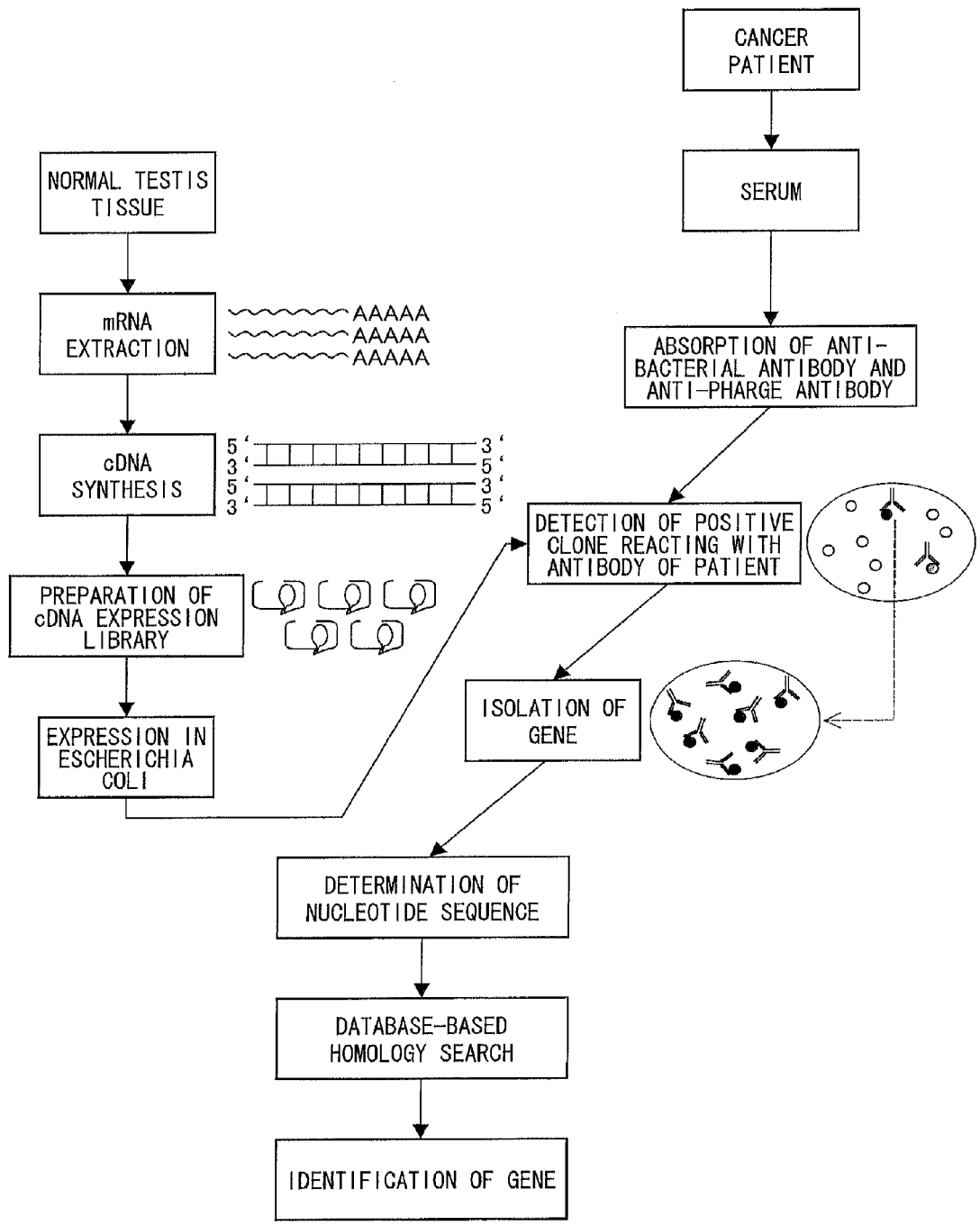
FIG. 1 is a view schematically showing SEREX.

The inventors of the present invention carried out SEREX for a cDNA library derived from normal testis using a serum from a specific patient with gastric cancer. As a result of SEREX, we found out that a positive clone was a clone expressing CCDC62 and that anti-CCDC62 antibody existed in the serum from the patient with gastric cancer. That is, the inventors of the present invention found out that CCDC62 was a cancer antigen in a patient with gastric cancer. Further, the inventors of the present invention carried out analysis of CCDC62 expression and confirmed that CCDC62 was strongly expressed only in testis among human normal tissues and also was expressed in cancer tissues and cancer cell lines. On the basis of these findings, the inventors of the present invention accomplished the present invention using the CT antigen, CCDC62.

SEREX (serological analysis of cancer antigens by recombinant cDNA expression cloning) is a method for identifying an antigen gene recognized by an antibody that exists in a patient serum from a cDNA expression library derived from cancer tissue (Sahin U, Tureci O, Schmitt H, Cochlovius B, Johannes T, Schmits R, Stenner F, Luo G, Schobert I, Pfreundschuh M. Human neoplasms elicit multiple specific immune responses in the autologous host. Proc Natl Acad Sci USA. 1995 Dec. 5; 92(25):11810-3). SEREX is known as an excellent method for screening a cancer antigen. It should be noted that the present invention, for the first time, provided the accomplishment using the cDNA library derived from normal testis, not using a cDNA library derived from autologous cancer tissue.

As above, the sequence of human CCDC62 is known, but the relevance of human CCDC62 to a disease has not been reported at all. The inventors of the present invention first found out the expression of CCDC62 in cancers and the presence of the anti-CCDC62 antibody in a serum from a cancer patient.

SEQ ID No: 1 represents a nucleotide sequence of transcript variant 1 of the human CCDC62 gene. SEQ ID No: 2 represents an amino acid sequence of a protein coded by transcript variant 1 of the human CCDC62 gene. SEQ ID No: 3 represents a nucleotide sequence of transcript variant 2 of the human CCDC62 gene. SEQ ID No: 4 represents an amino acid sequence of a protein coded by transcript variant 2 of the human CCDC62 gene. As for the nucleotide sequence of the human CCDC62 gene, transcript variant 1 and transcript variant 2 are registered respectively as NM_032573 and NM 201435 in the GenBank.

[1. A Method for Diagnosing a Cancer]

The present invention provides a method for diagnosing a cancer. In one embodiment, the cancer diagnostic method according to the present invention is a method for diagnosing a cancer by measuring the expression level of CCDC62 in a sample derived from a subject and then comparing the resultant expression level with a control level (e.g. normal level). More specifically, the cancer diagnostic method according to the present embodiment comprises a polynucleotide measuring step or a polypeptide measuring step. The expression level of CCDC62 can be determined by measuring the amount of transcripts (mRNA) or the amount of translation products (protein) by means of a technique known in the art.

In another embodiment, the cancer diagnostic method according to the present invention is a method for diagnosing cancer by measuring the level of the anti-CCDC62 antibody in a sample derived from a subject and then comparing the resultant level with a control level (e.g. normal level). More specifically, the cancer diagnostic method according to the present embodiment comprises an antibody measuring step. The level of the anti-CCDC62 antibody can be determined by measuring the level of the anti-CCDC62 antibody in a serum derived from the subject.

A subject objective to the cancer diagnostic method of the present invention, which is not particularly limited and includes a wide range of animals in general, is preferably a human. If the subject is a human, the subject can be not only a cancer patient and a patient suspected of having cancer but also a healthy person.

The sample derived from the subject used in the cancer diagnostic method of the present invention is not particularly limited as long as it is obtained from the subject (i.e. a sample separated from the subject). Examples of the sample include blood (serum, plasma, hemocyte, etc.), urine, feces, expectoration, ascites, peritoneal lavage fluid, biopsy tissue, and a surgically resected specimen.

The normal level means the expression level of CCDC62 mRNA, the expression level of CCDC62 protein, or the level of the anti-CCDC62 antibody in a normal healthy individual (healthy person). The normal level is preferably a measurement value obtained by using a normal cell, a normal tissue, or a normal body fluid as a sample that is of the same kind as the sample derived from the subject to be compared with (i.e. the sample used in the polynucleotide measuring step, the polypeptide measuring step, or the antibody measuring step of the present invention). Further, it is more preferable that the normal level is a mean value for the group consisting of normal healthy individuals.

As used herein, "diagnosis" encompasses not only "determination" but also "testing", "detection", and "prediction". That is, the diagnosis of a cancer means determination or prediction of whether a subject has a cancer, determination or prediction of a stage of cancer progression, and determination or prediction of a cancer treatment result, more preferably inspection/detection/prediction of whether a subject has a cancer, inspection/detection/prediction of a stage of cancer progression, and inspection/detection/prediction of a cancer treatment result.

The type of a cancer to be diagnosed is not particularly limited, but the cancer is preferably an epithelial tumor or a skin cancer. Examples of the epithelial tumor include a gastric cancer, a colon cancer, a breast cancer, a head and neck cancer, a lung cancer, a liver cancer, a renal cancer, an epithelial ovarian cancer, a prostatic cancer, and the like. Examples of the skin cancer include a malignant melanoma.

(1) Cancer Diagnostic Method Using mRNA Level as Index

In one embodiment, the cancer diagnostic method according to the present invention may be a method for diagnosing a cancer using a sample derived from a subject, the method including a polynucleotide measuring step of measuring the level of the presence of a polynucleotide including a nucleotide sequence of SEQ ID No: 1 or 3 or a partial sequence thereof in the sample derived from the subject. Note that the polynucleotide includes both DNA and RNA.

In the present embodiment, mRNA level of CCDC62 may be measured in the polynucleotide measuring step.

A method of measuring mRNA level, which is not particularly limited as long as it enables the measurement of a specific mRNA level, is selected for use as appropriate from among the known methods. Examples of the method of measuring mRNA level include a method using primers or a probe containing a polynucleotide consisting of nucleotide sequences of mRNAs or cDNAs of CCDC62 or a portion of complementary sequences of nucleotide sequences, wherein the polynucleotide is site-specifically bound to (hybridized with) any of mRNAs or cDNAs of CCDC62. The primers or probe may be subjected to various modifications for the measurement/detection of mRNA, as long as it forms site-specific base pairs with mRNA of CCDC62 or its corresponding cDNA.

The polynucleotide used as the above-described primers is not limited as long as it is designed on the basis of the nucleotide sequence of SEQ ID No: 1 or 3 or its complementary sequence. Examples of such a polynucleotide include a polynucleotide consisting of a nucleotide sequence of any of SEQ ID Nos: 5 through 8. These polynucleotides are the primers which were actually used by the inventors of the present invention in carrying out RT-PCR, and the polynucleotides are proved to specifically amplify cDNAs of CCDC62. The polynucleotide used as the above-described probe is not limited as long as it is designed on the basis of the nucleotide sequence of SEQ ID No: 1 or 3. Note that it is well known in the art that a polynucleotide available as primers that specifically amplify a mRNA (cDNA) of interest is usable as a probe for specifically detecting the mRNA (cDNA).

Examples of the known method of measuring mRNA using the primers or probe containing the polynucleotide site-specifically bound to the foregoing mRNA or cDNA include RT-PCR, real-time RT-PCR, competitive PCR, in situ hybridization, in situ PCR, DNA array method and the like.

For example, the above-described RT-PCR is a method of synthesizing cDNA, using reverse transcriptase, from total RNA or mRNA prepared from a sample, and then amplifying a region of interest by PCR using the synthesized cDNA as a template. Real-time RT-PCR is a method of, during amplification of a region of interest by PCR using cDNA as a template, monitoring in real time and analyzing the generation process of a resulting product of the amplification using a reagent for real-time monitoring. Examples of the reagent for real-time monitoring include SYBR (registered trademark: Molecular Probes Inc.) Green, TaqMan (registered trademark: Applied Biosystems Inc.) probe and the like.

For example, in the above-described DNA array method, cDNA or its fragment of CCDC62 is immobilized on a support and incubated with mRNA or cDNA prepared from a sample. At this time, the mRNA or cDNA may be labeled with a fluorescent dye or the like so that hybridization between the DNA immobilized on the support and the mRNA or cDNA prepared from the sample can be detected, and the mRNA level in the sample can be measured.

In the comparing step, the mRNA level of CCDC62 in the sample, which level has been measured in the polynucleotide measuring step, may be compared with the normal level. As described previously, the normal level is preferably measured by the same method using a normal cell, tissue, or body fluid, as a sample, that is of the same kind as the subject-derived sample to be compared (i.e. sample used in the polynucleotide measuring step of the present embodiment). The normal level may be obtained, concurrently with the polynucleotide measuring step, by measurement conducted for a sample derived from a normal and healthy individual, or may be data stored as background data. If mRNA level in the sample derived from the subject is higher than the normal level, it is possible to determine that the subject has a cancer. The level higher than the normal level is preferably a level twice higher than the normal level, more preferably a level three times higher than the normal level.

(2) Cancer Diagnostic Method Using Protein Level as Index

In one embodiment, the cancer diagnostic method according to the present invention may be a method for diagnosing a cancer using a sample derived from a subject, including a polypeptide measuring step of measuring the level of the presence of a polypeptide consisting of an amino acid sequence of SEQ ID No: 2 or 4 or a partial sequence thereof in the sample derived from the subject.

In the present embodiment, the level of CCDC62 protein may be measured in the polypeptide measuring step.

A method of measuring protein expression level, which is not particularly limited as long as it enables the measurement of a specific protein level, is selected for use as appropriate from among the known methods. Examples of the method of measuring protein expression level include a method using an antibody binding specifically to CCDC62 protein. The antibody may be a polyclonal antibody or a monoclonal antibody. Further, the antibody may be a complete antibody molecule or an antibody fragment capable of specifically binding (e.g. Fab fragment or F(ab')$_2$ fragment).

Examples of the known method of measuring a protein level using an antibody include radioimmunoassay (RIA), ELISA (enzyme linked immunoassay), Western blotting, immunoprecipitation method, immunohistochemical method, and antibody array method. Among these methods, ELISA is preferable in terms of high sensitivity and convenience.

In the comparing step, the level of the CCDC62 protein in the sample, which level has been measured in the polypeptide measuring step, may be compared with the normal level. As described previously, the normal level is preferably measured by the same method using a normal cell, tissue, or body fluid as a sample that is of the same kind as the subject-derived sample to be compared (i.e. sample used in the polypeptide measuring step of the present embodiment). The normal level may be obtained, concurrently with the polypeptide measuring step, by measurement conducted for a sample derived from a normal and healthy individual, or may be data stored as background data. If the protein level in the sample derived from the subject is higher than the normal level, it is possible to determine that the subject has cancer. The level higher than the normal level is preferably a level twice higher than the normal level, more preferably a level three times higher than the normal level.

(3) Cancer Diagnostic Method Using Antibody Level as Index

In one embodiment, the cancer diagnostic method according to the present invention may be a method for diagnosing a cancer using a sample derived from a subject, including an antibody measuring step of measuring the level of the presence of an antibody binding specifically to a polypeptide consisting of an amino acid sequence of SEQ ID No: 2 or 4 or a partial sequence thereof in the sample derived from the subject.

In the present embodiment, the level of anti-CCDC62 antibody may be measured in the antibody measuring step. Note that a sample used in measuring the level of the anti-CCDC62 antibody is preferably a serum, but is not particularly limited as long as it enables the measurement of the antibody level.

An antibody level measuring method is not particularly limited as long as it enables the measurement of a level of antibody titer against a specific antigen and the measurement using an antibody against an antibody of interest, and is selected for use as appropriate from among the known methods. Examples of the antibody level measuring method include ELISA using CCDC62 protein as an antigen and a protein array. The antigen protein used in measuring the antibody titer can be obtained by purification of a biological sample, but is preferably obtained as a recombinant protein. The recombinant protein can be obtained by introducing an expression vector including a CCDC62 gene into a host for expression and then purifying from the host.

In the comparing step, the level of the anti-CCDC62 antibody in the sample, which level has been measured in the antibody measuring step, may be compared with the normal level. The normal level may be obtained, concurrently with the antibody measuring step, by measurement conducted for a sample (preferably a serum) derived from a normal and healthy individual, or may be data stored as background data. If the level of the anti-CCDC62 antibody in the sample derived from the subject is higher than the normal level, it is possible to determine that the subject has a cancer. The level higher than the normal level is preferably a level twice higher than the normal level, more preferably a level three times higher than the normal level.

[2. Kit]

The present invention provides a kit used for diagnosis of cancers. The kit according to the present invention may include a reagent or an instrument required for implementation of the diagnostic method described previously. As used herein, the term "kit" refers to a packaging that includes a container (e.g. bottle, plate, tube, dish, etc.) storing a particular material therein. Preferably, the kit includes instructions for use of each reagent or instrument. As used herein concerning the kit, the term "includes (including)" refers to the inclusion of a reagent or an instrument in any one of individual containers that constitutes the kit. The "instructions" may be printed on a sheet of paper or other medium, or may be recorded in an electronic medium such as a magnetic tape, a computer-readable disk or tape, or a CD-ROM. The kit according to the present invention may further include a reagent or an instrument required for application to diagnosis of cancers.

In one embodiment, a kit according to the present invention can be a kit applicable to a cancer diagnostic method using the above-described mRNA level as an index. A kit according to the present embodiment may be a kit for diagnosing a cancer using a sample derived from a subject, the kit including a polynucleotide comprising a nucleotide sequence of SEQ ID No: 1 or 3 or a partial sequence thereof. Examples of the polynucleotide comprising a nucleotide sequence of SEQ ID No: 1 or 3 or a partial sequence thereof include primers and a probe both used for measurement of mRNA of CCDC62. The kit according to the present embodiment can be used suitably for measurement of a CCDC62 mRNA expression level.

A kit according to the present embodiment may be a RT-PCR kit for measurement of mRNA of CCDC62 or a real-time RT-PCR kit for measurement of mRNA of CCDC62. Further, a kit according to the present embodiment can be a kit by which RT-PCR or real-time RT-PCR can be carried out by user selection. In this case, a kit according to the present embodiment may include a primer pair for amplifying mRNA of CCDC62 by RT-PCR. Kit components other than the primer pair are not particularly limited. For example, the kit preferably includes a reagent for preparing RNA from tissues or cells, a reverse transcriptase, a buffer solution used for reverse transcription reaction, a heat-resistant DNA polymerase, a reagent for PCR, a reagent for real-time PCR, a tube for PCR, and a plate for PCR.

In another embodiment, a kit according to the present invention can be a kit applicable to a cancer diagnostic method using the above-described protein level as an index. A kit according to the present embodiment may be a kit for diagnosing a cancer using a sample derived from a subject, the kit including an antibody binding specifically to a polypeptide consisting of an amino acid sequence of SEQ ID No: 2 or 4 or a partial sequence thereof. The kit according to the present embodiment can be used suitably for measurement of CCDC62 protein level.

In yet another embodiment, a kit according to the present invention can be a kit applicable to a cancer diagnostic method using the above-described antibody level as an index. A kit according to the present embodiment may be a kit for diagnosing a cancer using a sample derived from a subject, the kit including a polypeptide consisting of an amino acid sequence of SEQ ID No: 2 or 4 or a partial sequence thereof. In this case, a kit according to the present embodiment can be used for measurement of a level of antibody titer of the anti-CCDC62 antibody. Further, a kit according to the present embodiment may include an antibody against the anti-CCDC62 antibody. A technique of preparing such an antibody is well known in the art.

A kit according to the present embodiment can be a kit for ELISA. Such a kit preferably includes either (i) an ELISA plate having an antibody binding specifically to the CCDC62 protein immobilized (solid-phased) thereon or (ii) an ELISA plate having the CCDC62 protein immobilized (solid-phased) thereon. Further, if a kit according to the present embodiment is a kit including both of the ELISA plates (i) and (ii), such a kit can be a kit capable of measuring both the CCDC62 protein level and the anti-CCDC62 antibody level.

Kit components other than the ELISA plate are not particularly limited. For example, a kit according to the present embodiment preferably includes a labeled secondary antibody, a coloring reagent, and a washing buffer solution.

Specific embodiments implemented in the description of the embodiments and the following examples only show technical features of the present invention and are not intended to limit the scope of the invention. Variations can be effected by a person skilled in the art within the spirit of the present invention and the scope of the following claims.

Further, all of scientific literatures and patent literatures listed herein are herein incorporated by reference.

EXAMPLES

The following will describe the present invention in more detail by way of Examples. It should be noted however that the present invention is not limited in any way by the following Examples. Unless otherwise specified, methods required for general genetic recombination, such as extraction, cleavage, and connection of nucleic acids, transformation of *Escherichia coli*, and determination of nucleotide sequence of a gene, are carried out according to a manual attached to a commercially-available reagent, equipment, and others for use in each operation and an experimental manual (e.g. "Molecular Cloning, a Laboratory Manual, 3rd Ed (Sambrook et al. (2001), Cold Spring Harbor Laboratory Press)").

Example 1

SEREX Analysis of Antigen Recognized by Antibody in Gastric Cancer Patient Serum As schematically shown in FIG. 1, SEREX is a method of searching for a cancer antigen using a serum from a cancer patient in a cDNA expression library prepared by direct extraction of mRNAs from a cancer tissue isolated from the cancer patient. In Example 1, a cancer-testis antigen useful for diagnosis of gastric cancer was isolated by SEREX using a cDNA library derived from normal testis and a serum from a patient with gastric cancer.

(1) Gastric Cancer Patient Serum

A serum was obtained from a patient with gastric adenocarcinoma whose primary lesion and liver metastasis both showed a tendency to reduce. The obtained serum was confirmed to strongly react with a protein fraction obtained from normal testis, before selected. The serum was diluted 10-fold with TBS (Tris-Buffered Saline) and then subjected to absorption of anti-bacterial antibodies (nonspecific antibodies against *Escherichia coli* and a phage) using an affinity column of *E. coli* Y1090/Y1089 (BioDynamics Lab Inc., Tokyo).

(2) Preparation of cDNA Expression Library

Using Quick Prep Micro mRNA purification kit (Stratagene, La Jolla, Calif., USA), mRNAs were purified from normal testis Total RNA (BD Biosciences Clontech, Palo Alto, Calif., USA). From 5 μg of mRNAs, cDNAs were synthesized. The cDNAs were then subcloned into γZAP Express vectors (Stratagene). The recombinant γZAP Express vectors were packaged into phages to prepare a cDNA expression library.

(3) Immunoscreening of Normal Testis cDNA Library

About 4,000 phages were planted on a 150 mm-plate and incubated for 6 to 8 hours. IPTG-induced protein was transferred into a 135 mm-diameter nitrocellulose membrane (Schleicher 86 Schuell, Dassel, Germany). Thereafter, the resultant membrane was reacted for 15 hours with the serum from the patient with gastric cancer (diluted 200-fold with TBS) absorbing the anti-bacterial antibodies, and then subjected to detection using a peroxidase-labeled anti-human IgG antibody (Jackson ImmunoResearch, West Grove, Pa., USA). At this time, in order to remove IgG clones derived from antibody production cells, the membrane was processed with a secondary antibody alone. Antibody-positive clones were isolated therefrom and then subjected to secondary screening and third screening using a 82 mm-diameter membrane and a 47 mm-diameter membrane, respectively, to obtain a single clone.

(4) Determination of Insert cDNA Nucleotide Sequence

The antibody-positive clone was converted into pBK-CMV plasmid by in vivo excision. Thereafter, a nucleotide sequence of insert cDNA was analyzed (ABI PRISM R310 Genetic Analyzer; PE Applied Biosystems, Foster City, Calif, USA), and homology search was carried out according to a gene database (www.ncbi.nih.gov/BLAST/Blast.cgi).

(5) Result

As a result of screening about 200,000 clones, fifty-five antibody-positive clones shown in Table 1 were isolated.

Example 2

Analysis of CCDC62 Expression

C62-1-S (sense: 5'-TCCCCGGCAAGTGAGCTAAT-3', SEQ ID No: 5) and C62-1-AS (antisense: 5'-ATACATC-CCCATTCCCGAGG-3', SEQ ID No: 6) as primers specific for CCDC62 (variant 1) and C62-2-S (sense: 5'-AAGTCA-GAGGTCCCAGAAGA-3', SEQ ID No: 7) and C62-2-AS (antisense: 5'-CTATGCAGGGGTTCTTTCTC-3', SEQ ID No: 8) as primers specific for CCDC62 (variant 2) were synthesized by a DNA synthesizer. By RT-PCR, cDNA derived from human normal tissues (MTC panel, BD Bio-

TABLE 1

SEREX-identified antigen genes

| Gene | No. of clones | Identity/similarities | Expression |
| --- | --- | --- | --- |
| OY-ST-1 | 10 | cytochrome b5 reductase 2 (CYB5R2), transcript variant 2 | Ubiquitous |
| OY-ST-2 | 8 | no homology | Testis |
| OY-ST-3 | 2 | G kinase anchoring protein 1 (GKAP1) | Testis |
| OY-ST-4 | 3 | pleckstrin and Sec7 domain containing 3 | Ubiquitous |
| OY-ST-5 | 4 | palladin, cytoskeletal associated protein | Ubiquitous |
| OY-ST-6 | 1 | synaptonemal complex protein 1, SYCP1 (SCP-1) | Testis |
| OY-ST-7 | 1 | ankyrin repeat domain 13B | Ubiquitous |
| OY-ST-8 | 1 | ATP synthase, H$^+$ transporting, mitochondrial F0 complex, subunit c (subunit 9) pseudogene 3 (ATP5GP3) on chromosome 14 | pseudogene |
| OY-ST-9 | 1 | lymphotoxin beta receptor (TNFR superfamily, member 3) | Ubiquitous |
| OY-ST-10 | 1 | leucine-rich repeats and calponin homology (CH) domain containing 4 | Ubiquitous |
| OY-ST-11 | 1 | heat shock transcription factor 2 | Ubiquitous |
| OY-ST-12 | 1 | MAX gene associated, transcript variant 8 (MGA) | Ubiquitous |
| OY-ST-13 | 4 | peroxisomal D3, D2-enoyl-CoA isomerase, transcript variant 1 | no data |
| OY-ST-14 | 7 | actin related protein ⅔ complex, subunit 2 34 kDa (ARPC2) | Ubiquitous |
| OY-ST-15 | 1 | suppressor of Ty 5 homolog (S. cerevisiae) (SUPT5H) | Ubiquitous |
| OY-ST-16 | 1 | polymerase (RNA) III (DNA directed) polypeptide H (22.9 KD) (POLR3H) | Ubiquitous |
| OY-ST-17 | 1 | centrosomal protein 290 kDa) (CEP290) | Ubiquitous |
| OY-ST-18 | 2 | coiled-coil domain containing 62 (CCDC62) | Testis |
| OY-ST-19 | 1 | dihydrouridine synthase 1-like (S. cerevisiae) | Ubiquitous |
| OY-ST-20 | 1 | leiomodin 1 (smooth muscle) (LMOD1) | Ubiquitous |
| OY-ST-21 | 1 | activating signal cointegrator 1 complex subunit 2 (ASCC2) | Ubiquitous |
| OY-ST-22 | 1 | chromosome 1 open reading frame 57 (C1orf57) | Ubiquitous |
| OY-ST-23 | 1 | F-box and leucine-rich repest protein 5 (FBXL5), transcript variant 1 | Ubiquitous |

As the result of the homology search, 23 kinds of genes (OY-ST-1 through OY-ST-23) were identified. Then, normal tissue expressions of these genes were searched according to the database. The result of the search showed that among these 23 kinds of genes 4 kinds of genes were specific to testis (Table 1). Regarding the other 19 kinds of genes, they were expressed in a broad area of normal tissue, or the data on their expressions was not obtained.

As genes expressing specifically in testis, 2 clones of OY-ST-3 (G kinase anchoring protein 1 (GKAP1)) were obtained. Regarding the invention concerning GKAP1, a patent application was filed by the same inventors of the present invention and is now pending (not published yet). Further, 1 clone of OY-ST-6 (synaptonemal complex protein 1, SYCP1 (SCP-1)) was obtained. SCP-1 (OY-ST-6), which is one of the typical cancer-testis antigens (CT antigens) discovered shortly after the development of SEREX, is known to have a weak immunogenicity (Tureci, et al., Proc. Natl. Acad. Sci. USA, 1998).

2 clones of OY-ST-18 were isolated, and the homology search showed that these 2 clones were CCDC 62 (coiled-coil domain containing 62), and that they were transcript variant 1 (CCDC62-1, NM_032573: SEQ ID No: 1) and transcript variant 2 (CCDC62-2, NM_201435: SEQ ID No: 3), respectively. It should be noted that it has not been reported that CCDC62 is related to diseases including human cancers.

sciences Clontech) and cDNAs derived from various cancers were amplified to analyze the expression of genes.

The cancer tissues as used were the donated ones that were obtained by a surgery or a biopsy. Note that all the samples derived from cancer patients or normal healthy individuals in Examples 1 and 2 were obtained by donation only from donors who had given informed consents after they had been directly given oral explanation and explanation in writing by their doctors in charge. The samples derived from cancer patients or normal healthy individuals were held anonymously and used in this study with their personal information strictly protected. The details of this study, an explanatory document for informed consent, and a certificate of informed consent were authorized by Okayama University, Graduate School of Medicine, Dentistry, and Pharmaceutical Sciences, Institutional Review Board of Human Genome and Gene Analysis Research.

Cancer cell lines as used were 11 kinds of lung cancer cell lines, 8 kinds of malignant melanoma cell lines, and 3 kinds of prostatic cancer cell lines. The malignant melanoma cell lines, which were established in the Sloane-Kettering Cancer Center in the U.S., were obtained therefrom by the inventors of the present invention. The other cell lines are commonly used for cancer research and usually available from a known cell preservation organization or the like.

From the cancer tissues and the cancer cell lines, respective total RNAs were extracted (RNeasy; Qiagen, Hilden, Germany). From the total RNAs, cDNAs were synthesized with MMLV reverse transcriptase and oligo(DT)$_{15}$ primers (Ready-To-Go You-Prime First-Strand Beads; Amersham Biosciences, Buckinghamshire, UK). RT-PCR for CCDC62 was carried out under the following conditions: 35 cycles of denaturation at 94° C. for 1 minute; annealing at 60° C. for 1 minute; and extension reaction at 72° C. for 1.5 minutes. The PCR products were analyzed by agarose gel electrophoresis. At the same time, the amplification of G3PDH gene from the synthesized cDNAs was confirmed.

Figure 2:
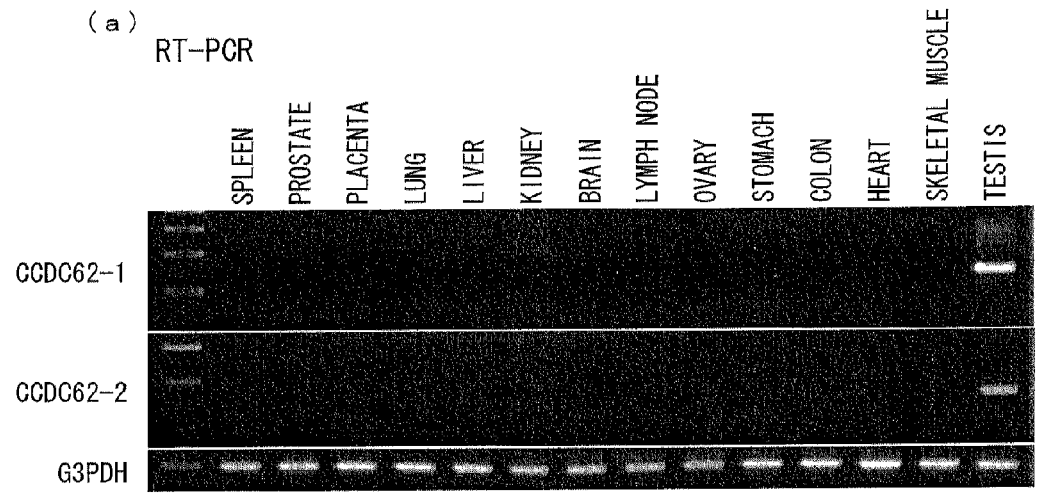
FIG. 2 is a view showing the result of analysis of CCDC62 mRNA expressions in human normal tissues, wherein (a) shows the result of RT-PCR analysis and (b) shows the result of real-time RT-PCR analysis.
Figure 2:
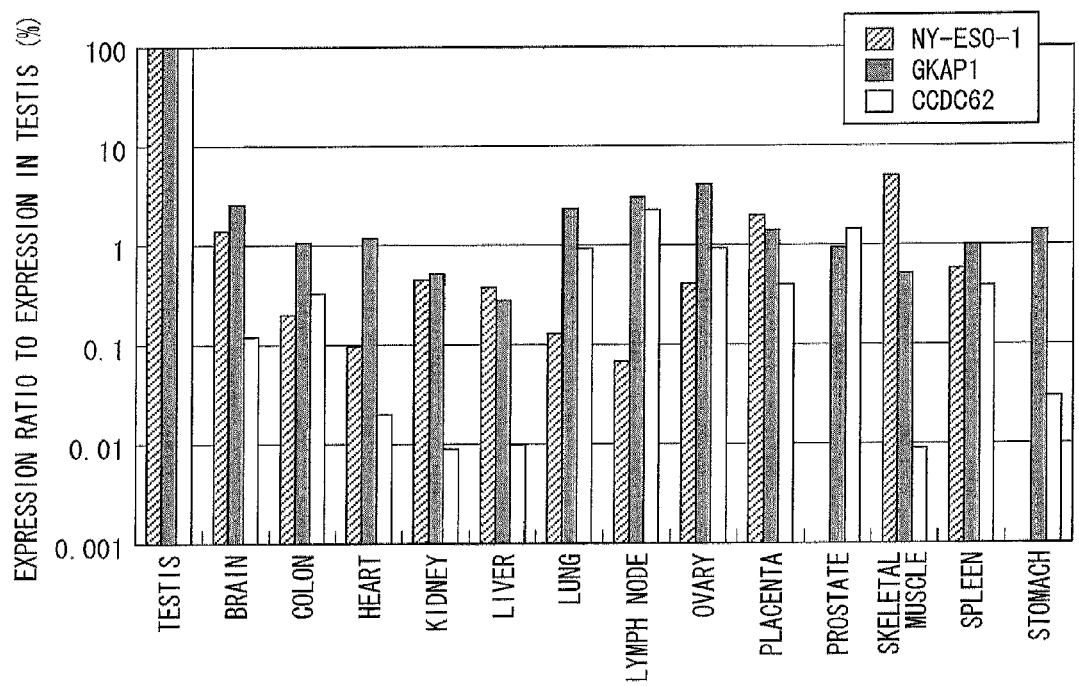

Regarding CCDC62-1 mRNA and CCDC62-2 mRNA, their expressions in 14 kinds of normal tissues were analyzed using CCDC62-1-specific primers or CCDC62-2-specific primers. The result of the analysis confirmed strong expressions in testis only ((a) of FIG. 2). The expression of CCDC62 genes in human normal tissues was quantitatively analyzed by real-time RT-PCR. Using random primers, cDNAs were synthesized from 2 μg of total RNAs (High-Capacity cDNA Reverse Transcription Kits, Applied Biosystems, Foster City, Calif.). Using CCDC62-specific TaqMan probe (TaqMan Gene Expression Assays, Applied Biosystems), the synthesized cDNAs were quantitatively analyzed with ABI PRISM 7700 Sequence Detection System (Applied Biosystems). The TaqMan probe (AssayID: Hs00261486) as used is a probe specific to a common sequence between 2 kinds of CCDC62 splice variants (CCDC62-1 and CCDC62-2). As an endogenous control, G3PDH was used (TaqMan Pre-Developed Assay Reagents, Applied Biosystems). The expression of CCDC62 was shown as compared with the expression of CCDC62 in normal testis, which was used as a calibrator. A strong CCDC62 expression in testis was confirmed. The level of such expression was equivalent to the level of expression of NY-ESO-1, which is a typical CT antigen, confirmed by the analysis carried out in the same procedure ((b) of FIG. 2).

The result of the analysis of CCDC62-1 mRNA and CCDC62-2 mRNA expressions in various cancer tissues showed no CCDC62-1 mRNA expressions. Table 2 shows the result of RT-PCR analysis of CCDC62-2 expression in various cancer tissues using specific primers.

TABLE 2

CCDC62-2 mRNA expressions
in cancer tissues and cancer cell lines (RT-PCR)

| Subject | Positive/total | |
|---|---|---|
| | Tissues | Cell lines |
| Breast cancer | 1/4 (25%) | ND |
| Colon cancer | 5/40 (12%) | ND |
| Esophageal cancer | 7/33 (21%) | ND |
| Gastric cancer | 8/117 (7%) | ND |
| Head and neck cancer | 4/34 (12%) | ND |
| Liver cancer | 0/5 (0%) | ND |
| Lung cancer | 5/19 (26%) | 4/11 (36%) |
| Ovarian cancer | 0/6 (0%) | ND |
| Prostate cancer | 3/9 (33%) | 1/3 (33%) |
| Renal cancer | 1/4 (25%) | ND |
| Malignant melanoma | ND | 3/8 (38%) |

Figure 3:
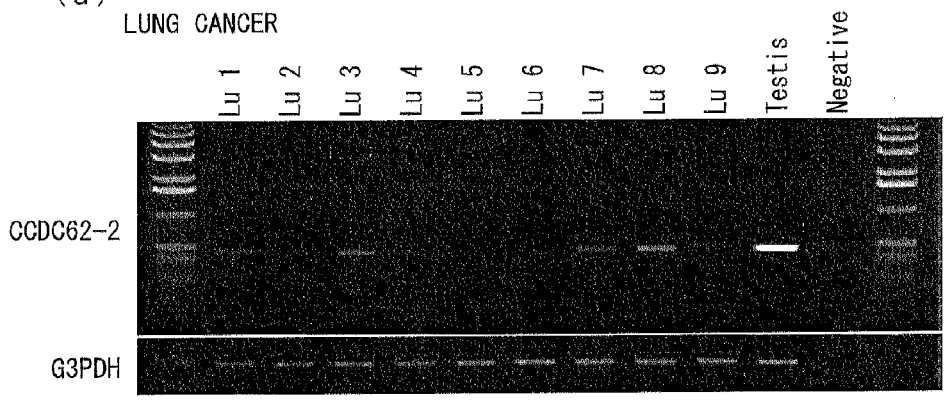
FIG. 3 is a view showing the result of RT-PCR analysis of CCDC62-2 mRNA expressions in various cancer tissues, wherein (a) shows the result of analysis for lung cancer and (b) shows the result of analysis for colon cancer, and (c) shows the result of analysis for prostatic cancer.
Figure 3:
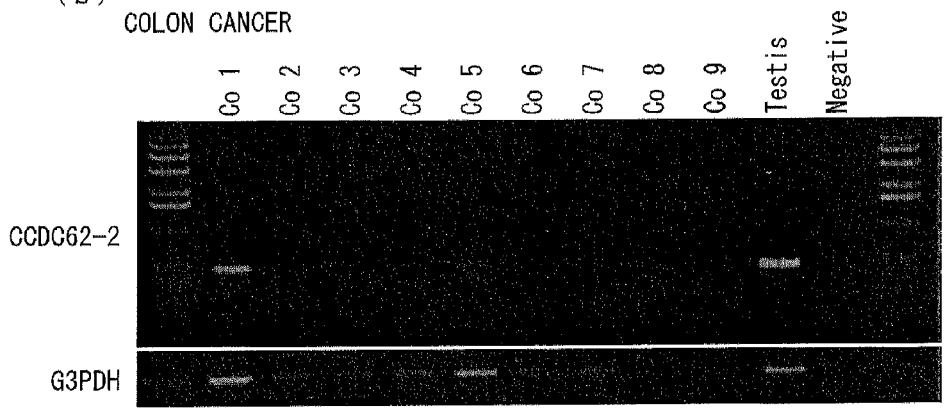
Figure 3:
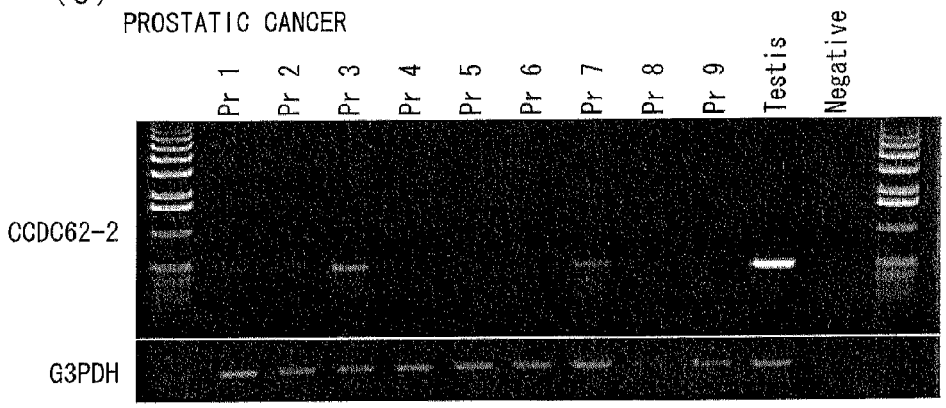

The CCDC62-2 mRNA expression was observed in an oral cavity cancer, an esophagus cancer, a gastric cancer, a breast cancer, a colon cancer, a lung cancer, a prostatic cancer, and a renal cancer (FIG. 3). Particularly, the CCDC62-2 mRNA expression in gastric cancer was confirmed in 8 of 117 cases (7%), the CCDC62-2 mRNA expression in lung cancer was confirmed in 5 of 19 cases (26%), and the CCDC62-2 mRNA expression in prostatic cancer was confirmed in 3 of 9 cases (33%). Further, the CCDC62-2 mRNA expression was also confirmed in cancer cell lines derived from lung cancer and prostatic cancer. Besides, high CCDC62-2 mRNA expression in malignant melanoma was confirmed in 3 of 8 cases (38%).

Example 3

Reactivity Against SEREX-Identified Antigens in Lung Cancer Patient Sera

Figure 4:
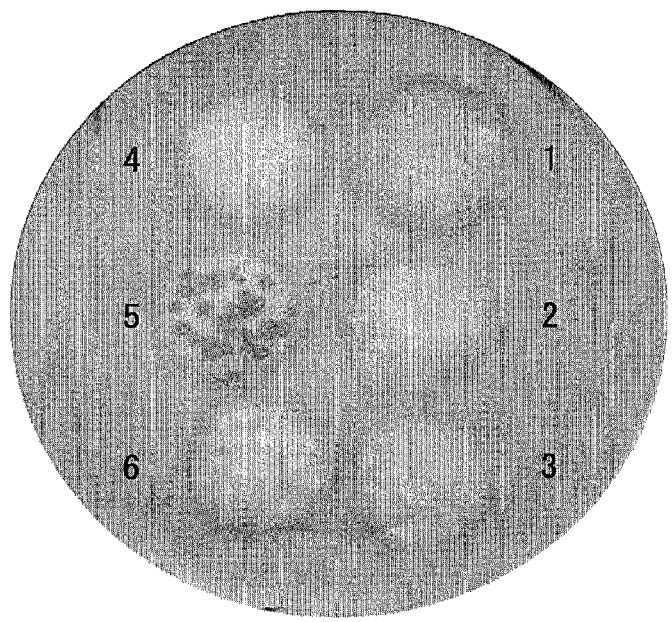
FIG. 4 is a view showing the result of analysis of reactivity of sera from patients with lung cancer against various antigens by phage plaque assay.

Reactivity of sera from lung cancer patients against CCDC62-1, CCDC62-2, and one more kind of identified CT antigen, GKAP1 clone was analyzed by phage plaque assay (FIG. 4).

TABLE 3

Reactivity against various antigens
in sera from lung cancer patients

| Antigen | Positive/total |
|---|---|
| OY-ST-2 (clone 1) | 6/29 |
| OY-ST-2 (clone 2) | 2/29 |
| CCDC62 (variant 1) | 0/29 |
| CCDC62 (variant 2) | 4/29 |
| GKAP1 | 2/29 |

Four out of 29 sera from patients with lung cancer were CCDC62-2 positive. Further, two out of 29 sera from patients with lung cancer were GKAP1-positive. Against CCDC62-1, none of the sera from patients with lung cancer reacted (Table 3). These antigens did not react with 7 healthy individual sera at all.

Example 4

Analysis of Humoral Immune Responses of Cancer Patients Against CCDC62-2 Protein Into pGEX-6P-1 expression vector, cDNA encoding C terminus (amino acid residue 366-684) of CCDC62-2 protein was inserted. *Escherichia coli* BL-21 was transformed with the vector. GST fused-CCDC62-2 protein, which had been obtained by IPTG induction, was purified using GSTrap FF column (Amersham Biosciences).

Humoral immune responses of cancer patients against CCDC62-2 were analyzed by ELISA ((a) of FIG. 5). Specifically, GST-fused recombinant CCDC62-2 protein (1 μg/ml) was adsorbed on a 96-well plate (100 ng per well), subjected to blocking with 5% FCS/PBS for 1 hour, and then reacted with the serum (100 μl) for 2 hours. After the plate was washed, the CCDC62-2 protein on the plate was reacted with peroxidase-labeled anti-human IgG antibody (Jackson ImmunoResearch) for 1 hour. The reactant was made colored with a substrate (1,2-phenylenediamine dihydrochloride). Thereafter, absorbance was measured for 191 of sera from cancer patients and 41 of sera from healthy individuals. Antibody titer was evaluated for 400-fold diluted sera, and an OD value not less than 4 SD, which corresponds to an average OD value (490 nm) of healthy individuals, was determined to be positive. The result is shown in Table 4.

TABLE 4

Detection of CCDC62-2-specific IgG antibody
in sera from cancer patients (ELISA analysis)

| Subject | Positive/total |
|---|---|
| Colon cancer | 2/11 (18%) |
| Gastric cancer | 6/104 (5.8%) |
| Lung cancer | 5/76 (6.6%) |
| Healthy donor | 0/41 (0%) |

Out of 191 cancer patients, 13 patients (6.8%) were antibody-positive. Forty-one healthy individuals examined were all negative. Out of 104 gastric cancer patients, 6 patients (5.8%) were antibody-positive. Out of 76 lung cancer patients, 5 patients (6.6%) were antibody-positive. Out of 11 colon cancer patients, 2 patients (18%) were antibody-positive.

Sera from patients with gastric cancer and sera from patients with lung cancer were examined by Western blotting ((b) of FIG. 5(b)). Specifically, the recombinant CCDC62-2 protein was separated by SDS-PAGE, transferred onto a nitrocellulose membrane, and then reacted with 100-fold diluted ELISA-positive and negative cancer patient sera. The protein after the reaction was detected using peroxidase-labeled anti-human IgG antibody (Jackson ImmunoResearch) to thereby analyze whether the antibodies in the sera were specific to the CCDC62-2 protein. The result of the analysis confirmed that the antibodies of the ELISA-positive patient sera were specific to the CCDC62-2 protein.

The present invention can provide a novel kit and method for diagnosing a cancer both using a CT antigen effective for diagnosis of digestive system cancer, such as gastric cancer and colon cancer. The CT antigen of interest is effectively used for not only diagnosis of digestive system cancer but also diagnosis of other epithelial tumors, such as breast cancer, head and neck cancer, lung cancer, renal cancer, and prostatic cancer, and diagnosis of skin cancer, such as malignant melanoma.

Specific embodiments or examples implemented in the description of the embodiments only show technical features of the present invention and are not intended to limit the scope of the invention. Variations can be effected within the spirit of the present invention and the scope of the following claims.

Industrial Applicability

The present invention can provide panels of a cancer antigen gene, a vector, a protein, an antibody, and cytotoxic T cell (CTL), and the like, for use in testing or diagnosis of cancer (determination of the presence or absence of cancer and a stage of cancer progression or prognostication of a cancer patient), prevention of cancer, treatment of cancer (e.g. vaccine against cancer), or the like. With these used alone or in combination or used as a kit, it is possible to evaluate a malignancy grade of cancer, a form of cancer tissue, treatment result, and prognostication. The use of CCDC62 enables a testing for cancer or a diagnosis of cancer with high accuracy. Moreover, in combination with CT antigens previously identified by the inventors of the present invention (e.g. OY-TES-1, RFX4, AKAP3, XAGE-1, and GKAP1), CCDC62 enables application to a wider variety of cancers.

The present invention is provided for use in diagnosis of cancer, and the present invention can be not only conductive to advances in medical sciences and medical care objective to cancers but also applicable to clinical test agent industry, reagent industry, medical equipment industry, and the like industries.

The invention claimed is:

1. A method for diagnosing an epithelial tumor or a melanoma, comprising:

mixing a sample derived from a subject and a polypeptide consisting of an amino acid sequence of position 366 to position 684 of SEQ ID No: 4, and measuring a level of an antibody binding specifically to the polypeptide in the sample.

2. The method according to claim 1, the method being used for diagnosis of at least one cancer selected from the group consisting of a gastric cancer, a colon cancer, a breast cancer, a head and neck cancer, a lung cancer, a renal cancer, a prostatic cancer, and a malignant melanoma.

3. The method according to claim 1, the antibody measuring step further comprising detecting an antibody which binds to the polypeptide.

4. The method according to claim 1, wherein the sample is sera.

5. The method according to claim 1, further comprising a step of comparing the level of the antibody binding specifically to the polypeltide obtained by the measuring with a control level.

* * * * *

SEQUENCE LISTING

<160> NUMBER OF SEQ ID NOS: 8

<210> SEQ ID NO 1
<211> LENGTH: 2481
<212> TYPE: DNA
<213> ORGANISM: human

<400> SEQUENCE: 1

```
ggttggagta cggggcgggg gtcggccgag ggcgcggggc cccggggctc cgggctcgcc      60
cccgccgctc ggggcaggcg cgccgatggc gtttctgagg tgacgccgcc cacaccgggc     120
ttctccgggg gcggaggaaa cacctatgaa ccctccggca gccttccttg ccgggcgcca     180
gaacatcggg tcagaagttg agatttccac tatcgagaaa caacggaagg agctgcagtt     240
gctcattgga gaattaaaag atcgagataa agagctcaat gacatggttg cagtgcacca     300
gcaacagctt ctttcatggg aagaggatcg gcagaaagtg ttgacactgg aagaacgttg     360
cagcaaatta gaaggtgaac tacataaaag aactgaaata atcaggtcac tcacgaagaa     420
ggtaaaagct cttgaatcca atcaaatgga atgccaaaca gctctccaaa agacccaact     480
acagcttcag gaaatggctc aaaaggcaac gcattcttct cttctctctg aagaccttga     540
ggctagaaac gaaactctca gcaacacgtt agtggaactt tctgcccagg taggacagct     600
acaagctcga gaacaagctc ttacgacaat gataaagcta aaggacaaag atattattga     660
ggcagttaat cacattgcag attgttcggg taaatttaaa atgctagagc atgccctacg     720
tgatgccaag atggcggaga cttgtattgt gaaagaaaag caagattata agcagaaatt     780
```

```
gaaggcactt aagattgaag tcaacaaact aaaagaggac ctcaatgaaa agacgacaga    840
aaataatgag caacgagaag agatcattcg cctcaagcaa gagaaaagtt gcctgcacga    900
tgaattgctt tttactgtag agagagaaaa gaggaaagat gaattgctta atattgcgaa    960
gtcaaagcaa gaacgcacaa attcagaact gcacaatctg agacagattt atgtaaaaca   1020
acagagtgat ctgcagtttc ttaatttcaa tgtggaaaat tctcaggaat taatacagat   1080
gtatgactca aagatggagg aatcaaaggc tctggactcc agcagagaca tgtgtttatc   1140
agaccttgaa aataaccacc caaaagtcga tattaagagg gaaaaaaatc agaagtcact   1200
gtttaaggac cagaaatttg aagccatgtt ggttcagcaa aataggtcag acaagagctc   1260
ttgcgatgaa tgcaaagaga gaaacaaca gatcgatact gtgtttgggg agaaaagtgt   1320
aattacgctg tcatccatat tcaccaaaga cttagtagag aaacacaacc tcccttggtc   1380
tctgggagga aaacccaga ttgaacccga aaacaaaatt acattgtgca agatccacac   1440
aaaatcacca aaatgtcatg gcactggggt tcagaacgaa ggaaaacaac cctcagaaac   1500 acccactta tctgatgaga agcagtggca tgatgtcagt gtttacctgg gcctgaccaa   1560
ctgtccaagt tcaaaacatc cagaaaagct ggatgtagaa tgtcaagatc agatggaaag   1620
gtccgaaatc tcatgctgcc agaaaaatga agcctgtctg ggcgaaagtg gcatgtgtga   1680
ctccaagtgc tgccacccga gtaacttcat aattgaagcc ccaggccaca tgtctgacgt   1740
ggagtggatg agtattttca agccttccaa aatgcagaga attgtccgcc tcaaatctgg   1800
gtgcacctgt tcagaaagca tctgtggcac acaacatgac tccccggcaa gtgagctaat   1860
tgccatccaa gattcccact ctttgggttc ttcaaaatct gccttgagag aagatgagac   1920
ggagtcctct tccaataaaa agaactcacc tacgagtttg ttaatctaca agatgcacc   1980 agcattcaat gaaaaggctt caattgtgtt accctcccag gatgatttct cgcccacgag   2040
caagctccag cgtttgctgg cggaatctcg tcagatggtg acggacctgg agctgagcac   2100
actgctgccc atcagccatg agaatctcac tggcagtgcc acaaatattt ctcatctatg   2160
tggaaggcag aaagcagaca ccaatactga atgaatactt aaccgtaaaa ctgaaagagg   2220
attctagttc ttcataaacg gcacttaatt ccagctggga gcagaactag aaagttaatt   2280
tttaaacatc tacacttcat tttcaagtta accattttg tgctgaagaa atattttcat   2340
gtgagtaaaa taaggaagga acgttcatca ctttaaactg aacctggcaa gttaatttcc   2400
tcgggaatgg ggatgtattt ttttaagcat tgcagatatc aaagttctat tgtgctgaat   2460
aaatgcccct tgttaacag g                                              2481
```

<210> SEQ ID NO 2
<211> LENGTH: 682
<212> TYPE: PRT
<213> ORGANISM: human

<400> SEQUENCE: 2

Met Asn Pro Pro Ala Ala Phe Leu Ala Gly Arg Gln Asn Ile Gly Ser
1               5                   10                  15

Glu Val Glu Ile Ser Thr Ile Glu Lys Gln Arg Lys Glu Leu Gln Leu
            20                  25                  30

Leu Ile Gly Glu Leu Lys Asp Arg Asp Lys Glu Leu Asn Asp Met Val
        35                  40                  45

Ala Val His Gln Gln Gln Leu Leu Ser Trp Glu Glu Asp Arg Gln Lys
    50                  55                  60

Val Leu Thr Leu Glu Glu Arg Cys Ser Lys Leu Glu Gly Glu Leu His
65                  70                  75                  80

-continued

```
Lys Arg Thr Glu Ile Ile Arg Ser Leu Thr Lys Val Lys Ala Leu
                85                  90                  95
Glu Ser Asn Gln Met Glu Cys Gln Thr Ala Leu Gln Lys Thr Gln Leu
            100                 105                 110
Gln Leu Gln Glu Met Ala Gln Lys Ala Thr His Ser Ser Leu Leu Ser
            115                 120                 125
Glu Asp Leu Glu Ala Arg Asn Glu Thr Leu Ser Asn Thr Leu Val Glu
        130                 135                 140
Leu Ser Ala Gln Val Gly Gln Leu Gln Ala Arg Glu Gln Ala Leu Thr
145                 150                 155                 160
Thr Met Ile Lys Leu Lys Asp Lys Asp Ile Glu Ala Val Asn His
                165                 170                 175
Ile Ala Asp Cys Ser Gly Lys Phe Lys Met Leu Glu His Ala Leu Arg
            180                 185                 190
Asp Ala Lys Met Ala Glu Thr Cys Ile Val Lys Glu Lys Gln Asp Tyr
        195                 200                 205
Lys Gln Lys Leu Lys Ala Leu Lys Ile Glu Val Asn Lys Leu Lys Glu
210                 215                 220
Asp Leu Asn Glu Lys Thr Thr Glu Asn Asn Glu Gln Arg Glu Glu Ile
225                 230                 235                 240
Ile Arg Leu Lys Gln Glu Lys Ser Cys Leu His Asp Glu Leu Leu Phe
            245                 250                 255
Thr Val Glu Arg Glu Lys Arg Lys Asp Glu Leu Leu Asn Ile Ala Lys
        260                 265                 270
Ser Lys Gln Glu Arg Thr Asn Ser Glu Leu His Asn Leu Arg Gln Ile
        275                 280                 285
Tyr Val Lys Gln Gln Ser Asp Leu Gln Phe Leu Asn Phe Asn Val Glu
    290                 295                 300
Asn Ser Gln Glu Leu Ile Gln Met Tyr Asp Ser Lys Met Glu Glu Ser
305                 310                 315                 320
Lys Ala Leu Asp Ser Ser Arg Asp Met Cys Leu Ser Asp Leu Glu Asn
                325                 330                 335
Asn His Pro Lys Val Asp Ile Lys Arg Glu Lys Asn Gln Lys Ser Leu
            340                 345                 350
Phe Lys Asp Gln Lys Phe Glu Ala Met Leu Val Gln Gln Asn Arg Ser
        355                 360                 365
Asp Lys Ser Ser Cys Asp Glu Cys Lys Glu Lys Gln Gln Ile Asp
    370                 375                 380
Thr Val Phe Gly Glu Lys Ser Val Ile Thr Leu Ser Ser Ile Phe Thr
385                 390                 395                 400
Lys Asp Leu Val Glu Lys His Asn Leu Pro Trp Ser Leu Gly Gly Lys
                405                 410                 415
Thr Gln Ile Glu Pro Glu Asn Lys Ile Thr Leu Cys Lys Ile His Thr
            420                 425                 430
Lys Ser Pro Lys Cys His Gly Thr Gly Val Gln Asn Glu Gly Lys Gln
        435                 440                 445
Pro Ser Glu Thr Pro Thr Leu Ser Asp Glu Lys Gln Trp His Asp Val
    450                 455                 460
Ser Val Tyr Leu Gly Leu Thr Asn Cys Pro Ser Ser His Pro Glu
465                 470                 475                 480
Lys Leu Asp Val Glu Cys Gln Asp Gln Met Glu Arg Ser Glu Ile Ser
                485                 490                 495
Cys Cys Gln Lys Asn Glu Ala Cys Leu Gly Glu Ser Gly Met Cys Asp
```

```
            500             505             510
Ser Lys Cys Cys His Pro Ser Asn Phe Ile Ile Glu Ala Pro Gly His
        515                 520                 525

Met Ser Asp Val Glu Trp Met Ser Ile Phe Lys Pro Ser Lys Met Gln
    530                 535                 540

Arg Ile Val Arg Leu Lys Ser Gly Cys Thr Cys Ser Glu Ser Ile Cys
545                 550                 555                 560

Gly Thr Gln His Asp Ser Pro Ala Ser Glu Leu Ile Ala Ile Gln Asp
                565                 570                 575

Ser His Ser Leu Gly Ser Ser Lys Ser Ala Leu Arg Glu Asp Glu Thr
                580                 585                 590

Glu Ser Ser Ser Asn Lys Lys Asn Ser Pro Thr Ser Leu Leu Ile Tyr
                595                 600                 605

Lys Asp Ala Pro Ala Phe Asn Glu Lys Ala Ser Ile Val Leu Pro Ser
        610                 615                 620

Gln Asp Asp Phe Ser Pro Thr Ser Lys Leu Gln Arg Leu Leu Ala Glu
625                 630                 635                 640

Ser Arg Gln Met Val Thr Asp Leu Glu Leu Ser Thr Leu Leu Pro Ile
                645                 650                 655

Ser His Glu Asn Leu Thr Gly Ser Ala Thr Asn Ile Ser His Leu Cys
                660                 665                 670

Gly Arg Gln Lys Ala Asp Thr Asn Thr Glu
        675                 680

<210> SEQ ID NO 3
<211> LENGTH: 3044
<212> TYPE: DNA
<213> ORGANISM: human

<400> SEQUENCE: 3
ggttggagta cggggcgggg gtcggccgag ggcgcgggc cccggggctc cgggctcgcc      60
cccgccgctc ggggcaggcg cgccgatggc gtttctgagg tgacgccgcc cacaccgggc     120
ttctccgggg gcggaggaaa cacctatgaa ccctccggca gccttccttg ccgggcgcca     180
gaacatcggg tcagaagttg agatttccac tatcgagaaa caacggaagg agctgcagtt     240
gctcattgga gaattaaaag atcgagataa agagctcaat gacatggttg cagtgcacca     300
gcaacagctt ctttcatggg aagaggatcg gcagaaagtg ttgacactgg aagaacgttg     360
cagcaaatta gaaggtgaac tacataaaag aactgaaata atcaggtcac tcacgaagaa     420
ggtaaaagct cttgaatcca atcaaatgga atgccaaaca gctctccaaa agacccaact     480
acagcttcag gaaatggctc aaaaggcaac gcattcttct cttctctctg aagaccttga     540
ggctagaaac gaaactctca gcaacacgtt agtggaactt ctgcccagg taggacagct     600
acaagctcga gaacaagctc ttacgacaat gataaagcta aaggacaaag atattattga     660
ggcagttaat cacattgcag attgttcggg taaatttaaa atgctagagc atgccctacg     720
tgatgccaag atggcggaga cttgtattgt gaaagaaaag caagattata agcagaaatt     780
gaaggcactt aagattgaag tcaacaaact aaaagaggac ctcaatgaaa agacgacaga     840
aaataatgag caacgagaag agatcattcg cctcaagcaa gagaaagtt gcctgcacga     900
tgaattgctt tttactgtag agagagaaaa gaggaaagat gaattgctta atattgcgaa     960
gtcaaagcaa gaacgcacaa attcagaact gcacaatctg agacagattt atgtaaaaca    1020
acagagtgat ctgcagtttc ttaatttcaa tgtggaaaat tctcaggaat taatacagat    1080
gtatgactca agatggagg aatcaaaggc tctggactcc agcagagaca tgtgtttatc    1140
```

| | |
|---|---|
| agaccttgaa aataaccacc caaaagtcga tattaagagg gaaaaaaatc agaagtcact | 1200 |
| gtttaaggac cagaaatttg aagccatgtt ggttcagcaa ataggtcag acaagagctc | 1260 |
| ttgcgatgaa tgcaaagaga agaaacaaca gatcgatact gtgtttgggg agaaaagtgt | 1320 |
| aattacgctg tcatccatat tcaccaaaga cttagtagag aaacacaacc tcccttggtc | 1380 |
| tctggggaga aaaacccaga ttgaacccga aaacaaaatt acattgtgca agatccacac | 1440 |
| aaaatcacca aatgtcatg gcactggggt tcagaacgaa ggaaaacaac cctcagaaac | 1500 |
| acccacttta tctgatgaga agcagtggca tgatgtcagt gtttacctgg gcctgaccaa | 1560 |
| ctgtccaagt tcaaaacatc cagaaaagct ggatgtgaa tgtcaagatc agatggaaag | 1620 |
| gtccgaaatc tcatgctgcc agaaaaatga agcctgtctg ggcgaaagtg gcatgtgtga | 1680 |
| ctccaagtgc tgccacccga gtaacttcat aattgaagcc ccaggccaca tgtctgacgt | 1740 |
| ggagtggatg agtattttca agccttccaa aatgcagaga attgtccgcc tcaaatctgg | 1800 |
| gtgcacctgt tcagaaagca tctgtggcac acaacatgac tccccggcaa gtgagctaat | 1860 |
| tgccatccaa gattcccact ctttgggttc ttcaaaatct gccttgagag aagatgagac | 1920 |
| ggagtcctct tccaataaaa agaactcacc tacgagtttg ttaatctaca aagatgcacc | 1980 |
| agcattcaat gaaaaggctt caattgtgtt accctcccag gatgatttct cgcccacgag | 2040 |
| caagctccag cgtttgctgg cggaatctcg tcagatggtg acggacctgg agctgagcac | 2100 |
| actgctgccc atcagccatg agaatctcac tggcagtgcc acaaataagt cagaggtccc | 2160 |
| agaagagtca gctcaaaaaa ataccttgt cagttattga aggaaacaaa aggcaacttc | 2220 |
| agtattcatc gtgatcacga atttctcatc tatgtggaag gcagaaagca gacaccaata | 2280 |
| ctgaatgaat acttaaccgt aaaactgaaa gaggattcta gttcttcata aacggcactt | 2340 |
| aattccagct gggagcagaa ctagaaagtt aattttttaaa catctacact tcattttcaa | 2400 |
| gttaaccatt tttgtgctga agaaatattt tcatgtgtaa gaaagtagac cttattgtac | 2460 |
| atatagaaag ttggaattat gctaagaatg aaaaagactt ctctgtaaag atacggacta | 2520 |
| cagttaaatg ctagagaagc tctttaaaaa tgtgaatgtc aaatagagaa agaacccctg | 2580 |
| catagaaagt gctgttttaa ctatctgatt tttaaaaaat ctgtgcatac atttaaattc | 2640 |
| taaacaatag cttatcagag tcagctcaaa atatatgaga aacagtattc tctcatggtt | 2700 |
| ttagcttttg actttgctgt gtaaatagac ataaggtgct ttgatataaa atataaaatg | 2760 |
| taactggaaa atagctcgag gtccttctgt cccaagctga gcagagcccc atctttctgg | 2820 |
| gtctatatta gtcccaccta ctgacacaaa caaaagcttg ctggaagatc gagttttaga | 2880 |
| cgcattttta aaaatcttaa agactaaaac acttccattt taacttgtaa agtaatttaa | 2940 |
| ttttttaaag attatactat atgcctctgt gtcttctcta aaagaataga tcaacttcag | 3000 |
| tccataaaag atattttaa tattaaagaa aaaaaaaaa aaaa | 3044 |

<210> SEQ ID NO 4
<211> LENGTH: 684
<212> TYPE: PRT
<213> ORGANISM: human

<400> SEQUENCE: 4

Met Asn Pro Pro Ala Ala Phe Leu Ala Gly Arg Gln Asn Ile Gly Ser
1               5                   10                  15

Glu Val Glu Ile Ser Thr Ile Glu Lys Gln Arg Lys Glu Leu Gln Leu
            20                  25                  30

Leu Ile Gly Glu Leu Lys Asp Arg Asp Lys Glu Leu Asn Asp Met Val

```
                35                  40                  45
Ala Val His Gln Gln Leu Leu Ser Trp Glu Glu Asp Arg Gln Lys
        50                  55                  60
Val Leu Thr Leu Glu Glu Arg Cys Ser Lys Leu Glu Gly Glu Leu His
 65                  70                  75                  80
Lys Arg Thr Glu Ile Ile Arg Ser Leu Thr Lys Val Lys Ala Leu
            85                  90                  95
Glu Ser Asn Gln Met Glu Cys Gln Thr Ala Leu Gln Lys Thr Gln Leu
                100                 105                 110
Gln Leu Gln Glu Met Ala Gln Lys Ala Thr His Ser Ser Leu Leu Ser
            115                 120                 125
Glu Asp Leu Glu Ala Arg Asn Glu Thr Leu Ser Asn Thr Leu Val Glu
        130                 135                 140
Leu Ser Ala Gln Val Gly Gln Leu Gln Ala Arg Glu Gln Ala Leu Thr
145                 150                 155                 160
Thr Met Ile Lys Leu Lys Asp Lys Asp Ile Ile Glu Ala Val Asn His
                165                 170                 175
Ile Ala Asp Cys Ser Gly Lys Phe Lys Met Leu Glu His Ala Leu Arg
            180                 185                 190
Asp Ala Lys Met Ala Glu Thr Cys Ile Val Lys Glu Lys Gln Asp Tyr
        195                 200                 205
Lys Gln Lys Leu Lys Ala Leu Lys Ile Glu Val Asn Lys Leu Lys Glu
    210                 215                 220
Asp Leu Asn Glu Lys Thr Thr Glu Asn Asn Glu Gln Arg Glu Glu Ile
225                 230                 235                 240
Ile Arg Leu Lys Gln Glu Lys Ser Cys Leu His Asp Glu Leu Leu Phe
                245                 250                 255
Thr Val Glu Arg Glu Lys Arg Lys Asp Glu Leu Leu Asn Ile Ala Lys
            260                 265                 270
Ser Lys Gln Glu Arg Thr Asn Ser Glu Leu His Asn Leu Arg Gln Ile
        275                 280                 285
Tyr Val Lys Gln Gln Ser Asp Leu Gln Phe Leu Asn Phe Asn Val Glu
    290                 295                 300
Asn Ser Gln Glu Leu Ile Gln Met Tyr Asp Ser Lys Met Glu Glu Ser
305                 310                 315                 320
Lys Ala Leu Asp Ser Ser Arg Asp Met Cys Leu Ser Asp Leu Glu Asn
                325                 330                 335
Asn His Pro Lys Val Asp Ile Lys Arg Glu Lys Asn Gln Lys Ser Leu
            340                 345                 350
Phe Lys Asp Gln Lys Phe Glu Ala Met Leu Val Gln Gln Asn Arg Ser
        355                 360                 365
Asp Lys Ser Ser Cys Asp Glu Cys Lys Glu Lys Gln Gln Ile Asp
    370                 375                 380
Thr Val Phe Gly Glu Lys Ser Val Ile Thr Leu Ser Ser Ile Phe Thr
385                 390                 395                 400
Lys Asp Leu Val Glu Lys His Asn Leu Pro Trp Ser Leu Gly Gly Lys
                405                 410                 415
Thr Gln Ile Glu Pro Glu Asn Lys Ile Thr Leu Cys Lys Ile His Thr
            420                 425                 430
Lys Ser Pro Lys Cys His Gly Thr Gly Val Gln Asn Glu Gly Lys Gln
        435                 440                 445
Pro Ser Glu Thr Pro Thr Leu Ser Asp Glu Lys Gln Trp His Asp Val
    450                 455                 460
```

-continued

Ser Val Tyr Leu Gly Leu Thr Asn Cys Pro Ser Ser Lys His Pro Glu
465                 470                 475                 480

Lys Leu Asp Val Glu Cys Gln Asp Gln Met Glu Arg Ser Glu Ile Ser
            485                 490                 495

Cys Cys Gln Lys Asn Glu Ala Cys Leu Gly Glu Ser Gly Met Cys Asp
        500                 505                 510

Ser Lys Cys Cys His Pro Ser Asn Phe Ile Ile Glu Ala Pro Gly His
        515                 520                 525

Met Ser Asp Val Glu Trp Met Ser Ile Phe Lys Pro Ser Lys Met Gln
530                 535                 540

Arg Ile Val Arg Leu Lys Ser Gly Cys Thr Cys Ser Glu Ser Ile Cys
545                 550                 555                 560

Gly Thr Gln His Asp Ser Pro Ala Ser Glu Leu Ile Ala Ile Gln Asp
                565                 570                 575

Ser His Ser Leu Gly Ser Ser Lys Ser Ala Leu Arg Glu Asp Glu Thr
            580                 585                 590

Glu Ser Ser Asn Lys Lys Asn Ser Pro Thr Ser Leu Leu Ile Tyr
        595                 600                 605

Lys Asp Ala Pro Ala Phe Asn Glu Lys Ala Ser Ile Val Leu Pro Ser
610                 615                 620

Gln Asp Asp Phe Ser Pro Thr Ser Lys Leu Gln Arg Leu Leu Ala Glu
625                 630                 635                 640

Ser Arg Gln Met Val Thr Asp Leu Glu Leu Ser Thr Leu Leu Pro Ile
                645                 650                 655

Ser His Glu Asn Leu Thr Gly Ser Ala Thr Asn Lys Ser Glu Val Pro
            660                 665                 670

Glu Glu Ser Ala Gln Lys Asn Thr Phe Val Ser Tyr
        675                 680

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: synthesized
      oligonucleotide

<400> SEQUENCE: 5
tccccggcaa gtgagctaat                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: synthesized
      oligonucleotide

<400> SEQUENCE: 6
atacatcccc attcccgagg                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: synthesized
      oligonucleotide

<400> SEQUENCE: 7
aagtcagagg tcccagaaga                                              20

```
<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: synthesized
      oligonucleotide

<400> SEQUENCE: 8
ctatgcaggg gttctttctc                                                  20
```